United States Patent [19]

Virnig et al.

[11] Patent Number: 4,639,540

[45] Date of Patent: Jan. 27, 1987

[54] DICYANOETHENYL FATTY COMPOUNDS AND DERIVATIVES THEREOF

[75] Inventors: Michael J. Virnig, Fridley; James P. Clark, St. Anthony, both of Minn.

[73] Assignee: Henkel Corporation, Minneapolis, Minn.

[21] Appl. No.: 706,540

[22] Filed: Feb. 28, 1985

[51] Int. Cl.[4] .......................................... C07C 121/30
[52] U.S. Cl. .................... 558/444; 558/451
[58] Field of Search ................ 260/465.6, 465.4; 558/444, 451

[56] References Cited

U.S. PATENT DOCUMENTS 2,818,434 12/1957 Vander Wal et al. ........ 260/465.6 X
3,093,557 6/1963 Cope, Jr. et al. ............ 260/465.6 X
4,216,343 8/1980 Rogier ................................. 568/853
4,243,818 1/1981 Rogier ................................. 560/224
4,356,128 10/1982 Rogier ............................. 260/465.6

OTHER PUBLICATIONS

Migrdichian, "The Chemistry of Organic Cyanogen Compounds", (1947), pp. 319, 328, 329, Reinhold Pub. Co.

*Primary Examiner*—Joseph Paul Brust
*Attorney, Agent, or Firm*—Ernest G. Szoke; John Daniel Wood; Patrick J. Span

[57] ABSTRACT

Dicyanoethenyl fatty compounds are provided which can be derivatized in a variety of ways to form a variety of compounds and polymeric products.

4 Claims, No Drawings

DICYANOETHENYL FATTY COMPOUNDS AND DERIVATIVES THEREOF

FIELD OF THE INVENTION

This invention relates to dicyanoethenyl substituted fatty compounds and to polymeric derivatives thereof. More particularly this invention relates to fatty acrylates that contain a dicyanoethenyl substituent, to the fatty alcohol precursors thereof, and to polymeric derivatives thereof derived by the addition polymerization of the dicyanoethenyl fatty acrylates.

BACKGROUND OF THE INVENTION

U.S. Pat. No. 4,356,128 to Rogier discloses that hydroxymethyl fatty nitriles, hydroxymethyl fatty amides, and hydroxymethyl fatty esters are useful as polyols for preparing polyurethane coatings and paints.

U.S. Pat. No. 4,216,343 to Rogier describes the preparation of hydroxymethyl fatty alcohols and the use thereof with polyisocyanates to form polyurethanes.

U.S. Pat. No. 4,243,818 to Rogier describes acrylate esters of gem-bis(hydroxymethyl) fatty alcohols and hydroxymethyl fatty alcohols and the use thereof in the preparation of radiation curable coatings.

SUMMARY OF THE INVENTION

This invention relates to compounds having the structural formula:

$$CH_3(CH_2)_m-(CH(HC=C(CN)_2))-(CH_2)_n-X$$

wherein:

X is hydroxyl or acryloxy, and
m and n are integers, provided that n is greater than 4 and the sum of m and n ranges from 8 to 20.

As used herein, the term "acryloxy" shall refer to a group having the structural formula:

$$-O-C(O)-CR=CH_2$$

wherein R is hydrogen or methyl.

The preferred compounds are those based on oleic acid and its derivatives, i.e. wherein m is 7 or 8, n is 8 or 9, and the sum of m and n is 16. The preferred compounds are also those based on acrylic acid, i.e. wherein R is hydrogen.

This invention also relates to derivatives of the above described dicyanoethenyl fatty acrylates, more particularly, polymers obtained by the addition polymerization of the dicyanoethenyl fatty acrylates.

DETAILED DESCRIPTION OF THE INVENTION

The following detailed description of this invention will describe the preparation of the dicyanoethenyl fatty acrylates of this invention, the starting materials used to prepare the dicyanoethenyl fatty acrylates of this invention, and the preparation of coatings by the addition polymerization of the dicyanoethenyl fatty acrylates of this invention.

A. Method of Preparing Dicyanoethenyl Fatty Acrylates

The preferred method of preparing the dicyanoethenyl fatty acrylates of this invention is described below.

The dicyanoethenyl fatty acrylates of this invention are prepared by reacting the corresponding dicyanoethenyl fatty alcohol with an acryloyl compound that is capable of esterifying the dicyanoethenyl fatty alcohol. The dicyanoethenyl fatty alcohols have the general formula:

$$CH_3-(CH_2)_m-(CH-(HC=C(CN_2))-(CH_2)_n-OH$$

wherein m and n are as previously defined. Methods of obtaining the dicyanoethenyl fatty alcohols are described above and exemplified below.

The acryloyl compounds used to esterify the dicyanoethenyl fatty alcohol is preferably an acryloyl halide, such as acryloyl chloride, but may be other reactive acryloyl compounds, such as acryloyl anhydride, acrylic acid or lower alkyl esters thereof.

The amount of acryloyl compound used to esterify the dicyanoethenyl fatty alcohol is not critical; generally an amount of the acryloyl compound in excess of 1 equivalent thereof should be used to ensure the full acrylation of the starting dicyanoethenyl fatty alcohol.

B. Preparation of Starting Materials

The dicyanoethenyl fatty alcohols described above are preferably prepared by hydroformylating an unsaturated fatty alcohol and by reacting the resulting formyl-substituted fatty alcohol with malononitrile as described below.

The formyl-substituted fatty compounds used in the preparation of the dicyanoethenyl fatty acrylates described above can be obtained by reacting an unsaturated fatty compound having the formula:

$$CH_3-(CH_2)_m-CH=CH-(CH_2)_n-X$$

wherein X is hydroxyl with carbon monoxide and hydrogen in the presence of a rhodium carbonyl catalyst. The particular techniques of obtaining the desired starting material are more particularly described in U.S. Pat. Nos. 4,216,343 and 4,356,128, the disclosures of which are incorporated herein by reference thereto.

The reaction of the formyl-substituted fatty compound with malononitrile is conducted in the presence of an alkaline reagent which serves to catalyze the addition of malononitrile to the formyl carbonyl to form a beta-hydroxysubstituted intermediate which is then dehydrated to form the dicyanoethenyl compounds of this invention. Examples of suitable alkaline reagents include organic amines, e.g. p-aminophenol. The reaction is also preferably conducted in the presence of a hydrocarbon solvent e.g. hexane. Techniques to remove water produced by the dehydration of the beta-hydroxy alcohol are also preferably employed. Such techniques include the removal of water as an azeotrope with an organic compound, e.g. hexane.

C. Coating Preparation

The dicyanoethenyl fatty acrylates of this invention will undergo addition polymerization to prepare polymeric derivatives thereof. The dicyanoethenyl fatty acrylates of this invention can be homopolymerized or mixed with other ethylenically unsaturated comonomers and then polymerized.

The addition polymerization of the dicyanoethenyl fatty acrylate can be accomplished on the surface of a substrate to form a polymeric coating. A composition of this invention is applied to a substrate such as wood, metal, paper, or plastics by any convenient method such as knife, blade, brush, or spray. The coated surface can then be exposed to radiation sufficient to cure the composition through the radiation sensitive pi bonds. Suitable sources of ionizing radiation include ultraviolet light or radioactive sources such as are described in U.S. Pat. No. 3,935,330 to Smith et al.

The coating can be cured by including in the composition free radical initiators such as be benzoin, benzoin ethers, and Michler's Ketone. Other suitable free radical initiators are organic peroxides, hydroperoxides, per acids, per esters, azo compounds, ditertiary butyl peroxide, benzoyl peroxide, 2,4-dichlorobenzoyl peroxide, tertiary butyl hydroperoxide, 2,5-dimethyl-2,5-bis(hydroperoxy)-hexane, peracetic acid, perbenzoic acid, tertiary butyl peroxypivalate, tertiary butyl peracetic acid and azo-bis-isobutyl nitrile. The free radical initiator may be present at from 0.01 to about 20% by weight of the radiation curable components.

To ensure that the composition does not polymerize prior to the application of the compound to a substrate, a free radical inhibitor may be added to the composition. Examples of suitable inhibitors include hydroquinone and the methyl ether thereof or butylated hydroxy toluene at a level of from about 5 ppm to about 2000 ppm by weight of the radiation curable components.

The amount of radiation necessary to cure the composition will of course depend upon the wavelength and intensity of the radiation, the angle of exposure to the radiation, the thickness of the coating to be applied, and the amount of dicyanoethenyl fatty acrylate in the coating composition as well as the presence or absence of a free radical initiating catalyst. For any given composition, experimentation to determine the amount of radiation sensitive pi bonds not cured following exposure to the radiation source is the best method of determining the amount and duration of the radiation required.

The coatings produced by the cure of the dicyanoethenyl fatty acrylates of this invention are useful in a wide variety of applications i.e. decorative, maintenance, or industrial coatings. For example, they can be used as binders in inks. In the electronics area, these materials have applications as non-conductive coatings, e.g. solder masks for circuit boards or moisture resistant coatings for circuit boards or optical fibers.

The use of the dicyanoethenyl fatty acrylates of this invention should provide excellent flexibility in the final coating and offer good compatibility with other compounds in the coating formulation. The presence of the polar nitrile functionality will also lead to improved surface wetting properties as compared with most commercially available curable coatings resulting in better adhesion to the substrate and improved pigment compatibility.

The dicyanoethenyl fatty alcohols should also have application as raw materials for the preparation of crosslinked polymers. The reaction of the dicyanoethenyl fatty alcohols and a polyol with polyfunctional organic compounds copolymerizable therewith, e.g. polybasic acids or polyisocyanates, will yield a dicyanoethenyl terminated copolymer, e.g. a polyester or a polyurethane, which can then be cured by the addition polymerization of the dicyanoethenyl groups to form a crosslinked polymer. These copolymers are especially useful when cured on a substrate to form a coating.

EXAMPLES

The following examples show the preparation of compounds representative of the compounds of this invention.

EXAMPLE 1

PREPARATION OF 9(10)-(DICYANOETHENYL)OCTADECAN-1-OL

Charge

| Materials | M.W. | Weight (g) | Moles |
| --- | --- | --- | --- |
| 9(10)-Formyloctadecanol | 298 | 1621 | 5.44 |
| Malononitrile | 66 | 377 | 5.71 |
| p-Aminophenol | 109 | 35 | 0.321 |
| Hexanes | — | 340 | — |

Equipment

A 5 liter three neck, round-bottom flask, fitted with a mechanical stirrer, thermometer, heating mantle, and Dean-Stark Itrap for azeotropic removal of water.

Procedure

The materials were placed in the flask and heated to reflux. After four hours, water evolution essentially stopped. The reaction mixture was cooled and then poured into an equal volume of toluene. The resultant organic was washed with 2% sulfuric acid (2 parts by volume organic to acid) and then water washed to neutrality. Removal of the solvent in vacuo gave approximately 1900 g of a dark oil. This oil was treated with 1 equivalent of sodium methoxide per equivalent of acid present and then wiped film evaporator distilled to give a water white oil. That the oil contained the desired products was confirmed by NMR spectroscopy.

EXAMPLE 2

PREPARTION OF 9(10)-(DICYANOETHENYL)OCTADECAN-1-YL ACRYLATE

Charge

| Materials | M.W. | Weight (g) | Moles |
| --- | --- | --- | --- |
| 9(10)-(Dicyanoethenyl)octadecan-1-ol | 346 | 150 | 0.43 |
| Acryloyl Chloride | 90 | 74.5 | 0.83 |
| Triethylamine | 101 | 83.2 | 0.82 |
| Phenothiazine | — | 0.1 | — |
| Dichloromethane | 84 | 662 | 7.88 |

Procedure

The reaction was run in the same fashion as described by Kulkarni, et al. [JAOCS, 46, p. 396–398 (1969)]. The reaction mixture was worked up in the following fashion. The dichloromethane was removed in vacuo and 800 ml of heptane were added to the flask. The heptane solution was cooled in a freezer overnight and then the triethylamine hydrochloride was removed by filtration. The resultant filtrate was transferred to a separatory funnel and washed twice with 600 ml of 2% sulfuric acid. A thick, emulsified aqueous phase separated in each case. These emulsions were combined and worked up separately. The acid washed organic was then water washed to neutrality with water, filtered, and the solvent removed in vacuo to yield 142.9 g. of a yellow oil. That the yellow oil contained the desired product was established by IR, NMR and GLC analysis.

The aqueous acid emulsions were worked up by extracting with dichloromethane. The resultant dichloromethane extract was then water washed to neutrality, filtered and the solvent removed in vacuo to yield an additional 66.7 g of product.

What is claimed is:

1. A dicyanoethenyl fatty compound having the structural formula:

$$CH_3(CH_2)_m-(CH(HC=C(CN)_2))-(CH_2)_n-OH$$

where m and n are integers, provided that n is greater than 4 and the sum of m and n ranges from 8 to 20.

2. A dicyanoethenyl fatty compound having the structural formula:

$$CH_3(CH_2)_m-(CH(HC=C(CN)_2))-(CH_2)_n-O-C(O)-CR=CH_2$$

wherein R is H or methyl, m and n are integers and provided that n is greater than 4 and the sum of m and n ranges from 8 to 20.

3. A compound in accordance with claim 1 wherein m is 7 or 8, n is 8 or 9 and the sum of m and n is 16.

4. A compound in accordance with claim 2 wherein m is 7 or 8, n is 8 or 9 and the sum of m and n is 16.

* * * * *